US00PP21507P2

(12) United States Plant Patent
Oudshoorn

(10) Patent No.: US PP21,507 P2
(45) Date of Patent: Nov. 16, 2010

(54) ***SEDUM* PLANT NAMED 'TWINKLING STAR'**

(50) Latin Name: *Hylotelephium spectabile*
Varietal Denomination: Twinkling Star

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/459,833

(22) Filed: Jul. 8, 2009

(51) Int. Cl.
*A01H 5/00* (2006.01)

(52) U.S. Cl. ..... Plt./479

(58) Field of Classification Search ..... Plt./479
See application file for complete search history.

*Primary Examiner*—June Hwu
(74) *Attorney, Agent, or Firm*—C. A. Whealy

(57) ABSTRACT

A new and distinct cultivar of *Sedum* plant named 'Twinkling Star', characterized by its upright and compact plant habit; freely basally branching habit; dense and bushy growth habit; attractive yellow green-colored flowers; and good garden performance.

2 Drawing Sheets

Botanical designation: *Hylotelephium spectabile.*
Cultivar denomination: 'TWINKLING STAR'.

BACKGROUND OF THE INVENTION

The present invention relates to a new and distinct cultivar of *Sedum* plant, botanically known as *Hylotelephium spectabile* and hereinafter referred to by the name 'Twinkling Star'.

The new *Sedum* plant is a product of a planned breeding program conducted by the Inventor in Rijpwetering, The Netherlands. The objective of the breeding program is to create new strong and healthy *Sedum* cultivars with numerous attractive flowers.

The new *Sedum* plant originated from a cross-pollination during the summer of 2004 in Rijpwetering, The Netherlands, of *Hylotelephium spectabile* 'Purple Emperor', not patented, as the female, or seed, parent with *Sedum telephium* 'Sunkissed', disclosed in U.S. Plant Pat. No. 16,927, as the male, or pollen, parent. The new *Sedum* was discovered and selected by the Inventor as a single flowering plant within the progeny of the stated cross-pollination in a controlled greenhouse environment in Rijpwetering, The Netherlands during the summer of 2005.

Asexual reproduction of the new *Sedum* plant by vegetative cuttings in a controlled environment in Rijpwetering, The Netherlands since the summer of 2005, has shown that the unique features of this new *Sedum* plant are stable and reproduced true to type in successive generations.

SUMMARY OF THE INVENTION

Plants of the new *Sedum* have not been observed under all possible environmental conditions. The phenotype may vary somewhat with variations in environment such as temperature and light intensity without, however, any variance in genotype.

The following traits have been repeatedly observed and are determined to be the unique characteristics of 'Twinkling Star'. These characteristics in combination distinguish 'Twinkling Star' as a new and distinct cultivar of *Sedum:*

1. Upright and compact plant habit.

2. Freely basally branching habit; dense and bushy growth habit.
3. Attractive yellow green-colored flower.
4. Good garden performance.

Plants of the new *Sedum* differ from plants of the female parent, 'Purple Emperor', primarily in flower color as plants of 'Purple Emperor' have pink-colored flowers.

Plants of the new *Sedum* differ from plants of the male parent, 'Sunkissed' primarily in leaf color as plants of 'Sunkissed' have green to greyed green-colored leaves.

Plants of the new *Sedum* can be compared to plants of *Sedum telephium* 'Bronco', disclosed in U.S. Plant Pat. No. 18,085. Plants of the new *Sedum* and 'Bronco' differ in the following characteristics:

1. Plants of the new *Sedum* are more compact than plants of 'Bronco'.
2. Plants of the new *Sedum* have darker yellow green-colored flowers than plants of 'Bronco'.

BRIEF DESCRIPTION OF THE PHOTOGRAPHS

The accompanying colored photographs illustrate the overall appearance of the new *Sedum* plant, showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of a typical flowering plant of 'Twinkling Star' grown in a container.

The photograph at the top of the second sheet is a close-up view of typical inflorescences of 'Twinkling Star'. The photograph at the bottom of the second sheet is a close-up view of a typical leaf of 'Twinkling Star'.

DETAILED BOTANICAL DESCRIPTION

The aforementioned photographs and following observations, measurements and values describe plants grown in Rijpwetering, The Netherlands, under commercial practice during the autumn in an outdoor nursery with day temperatures ranging from 12° C. to 25° C. and night temperatures ranging from 2° C. to 14° C. Plants used in the photographs and description were two years old. In the following description, color references are made to The Royal Horticultural Society Colour Chart, 2007 Edition, except where general terms of ordinary dictionary significance are used.

Botanical classification: *Sedum telephium* 'Twinkling Star'.

Parentage:

*Female, or seed, parent.*—*Hylotelephium spectabile* 'Purple Emperor', not patented.

*Male, or pollen, parent.*—*Hylotelephium spectabile* 'Sunkissed' disclosed in U.S. Plant Pat. No. 16,927.

Propagation:

*Type.*—By vegetative cuttings.

*Time to initiate roots.*—About 15 to 20 days at 18° C.

*Time to produce a rooted young plant.*—About two months at 16° C. to 22° C.

*Root description.*—Moderately thick and moderately fleshy; white to medium brown in color.

*Rooting habit.*—Moderately freely branching; moderately dense.

Plant description:

*Plant form/habit.*—Herbaceous perennial; upright and compact plant habit; broad inverted triangle; moderately vigorous growth habit; freely basally branching habit with about five basal branches developing per plant; dense and bushy growth habit.

*Plant height.*—About 14.8 cm.

*Plant width* (*spread*).—About 19.6 cm.

*Lateral branches.*—Length: About 6.4 cm. Diameter: About 5 mm. Internode length: About 3.7 cm. Strength: Strong. Texture: Smooth, glabrous. Color: Close to 145B.

Foliage description:

*Arrangement.*—Opposite, simple; sessile.

*Length.*—About 6.2 cm.

*Width.*—About 4.2 cm.

*Shape.*—Ovate.

*Apex.*—Bluntly acute to rounded.

*Base.*—Truncate.

*Margin.*—Irregularly and shallowly dentate.

*Texture, upper and lower surfaces.*—Smooth, glabrous; succulent.

*Venation pattern.*—Pinnate.

*Color.*—Developing leaves, upper surface: Close to 137A. Developing leaves, lower surface: Close to 191A to 191B. Fully expanded leaves, upper surface: Between N137C and 147A; venation, close to 143A. Fully expanded leaves, lower surface: Close to 191A; ventation, close to 144A to 144B.

Flower description:

*Flower type/habit.*—Small rotate flowers arranged in terminal compound cymes; flowers face upright to slightly outward; freely flowering habit with about 2,000 flower buds and flowers developing per plant.

*Fragrance.*—None detected.

*Natural flowering season.*—Continuously flowering from August to late October in The Netherlands.

*Postproduction longevity.*—Flowers last about two weeks on the plant; flowers persistent.

*Flower buds.*—Height: About 4 mm. Diameter: About 2 mm. Shape: Ovate. Color: Close to 145C to 145D; towards the apex, close to 181C to 181D; towards the base, close to 148C.

*Inflorescence height.*—About 6.2 cm.

*Inflorescence diameter.*—About 6.9 cm.

*Flower diameter.*—About 6 mm.

*Flower depth.*—About 5 mm.

*Petals.*—Quantity per flower: Typically five in a single whorl; petals fused at the base. Length: About 5 mm. Lobe width: About 2 mm. Shape: Ovate. Apex: Acute. Margin: Entire. Texture, upper and lower surfaces: Smooth, glabrous. Color: When opening, upper and lower surfaces: Close to 149D; towards the apex, close to 147B. Fully opened, upper and lower surfaces: Close to 149D; towards the apex, close to 147B.

*Sepals.*—Quantity per flower: Typically five in a single whorl, fused at the base. Length: About 2 mm. Width: About 1 mm. Shape: Narrowly ovate. Apex: Acute. Margin: Entire. Texture, upper and lower surfaces: Smooth, glabrous. Color: When opening, upper and lower surfaces: Close to 148C. Fully opened, upper and lower surfaces: Close to 148C.

*Peduncles.*—Length: About 4.9 cm. Diameter: About 3 mm. Angle: Erect to about 30° from vertical. Strength: Moderately strong. Texture: Smooth, glabrous. Color: Close to 145B.

*Pedicels.*—Length: About 3 mm. Diameter: About 0.7 mm. Angle: Erect to about 40° from vertical. Strength: Moderately strong. Texture: Smooth, glabrous. Color: Close to 148C.

*Reproductive organs.*—Stamens: Quantity per flower: Typically ten. Filament length: About 2.5 mm. Filament color: Close to 3D. Anther shape: Broadly oblong, flattened. Anther length: About 0.3 mm. Anther color: Close to 33A. Pollen amount: Scarce. Pollen color: Close to 12B to 12C. Pistils: Quantity per flower: Five. Pistil length: About 4 mm. Stigma shape: Pointed. Stigma color: Close to 1C. Style length: About 3 mm. Style color: Close to 1C. Ovary color: Close to 1C.

*Seed/fruit.*—Seed and fruit development have not been observed.

Disease/pest resistance: Plants of the new *Sedum* have not been noted to be resistant to pathogens and pests common to *Sedum*.

Garden performance: Plants of the new *Sedum* have been observed to have good garden performance and tolerate rain and wind. Plants of the new *Sedum* tolerate high temperatures of about 35° C. and are winter hardy to USDA Hardiness Zone 5.

It is claimed:

1. A new and distinct *Sedum* plant named 'Twinkling Star' as illustrated and described.

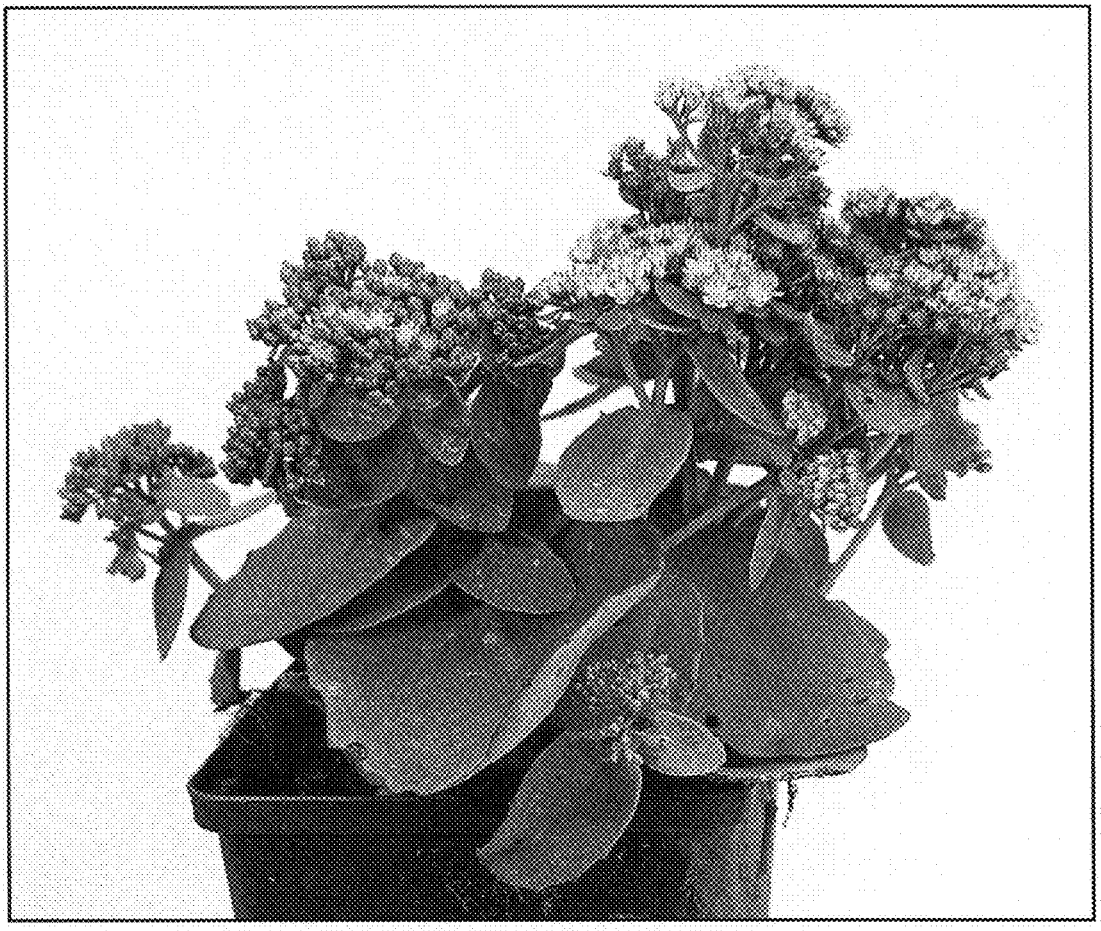

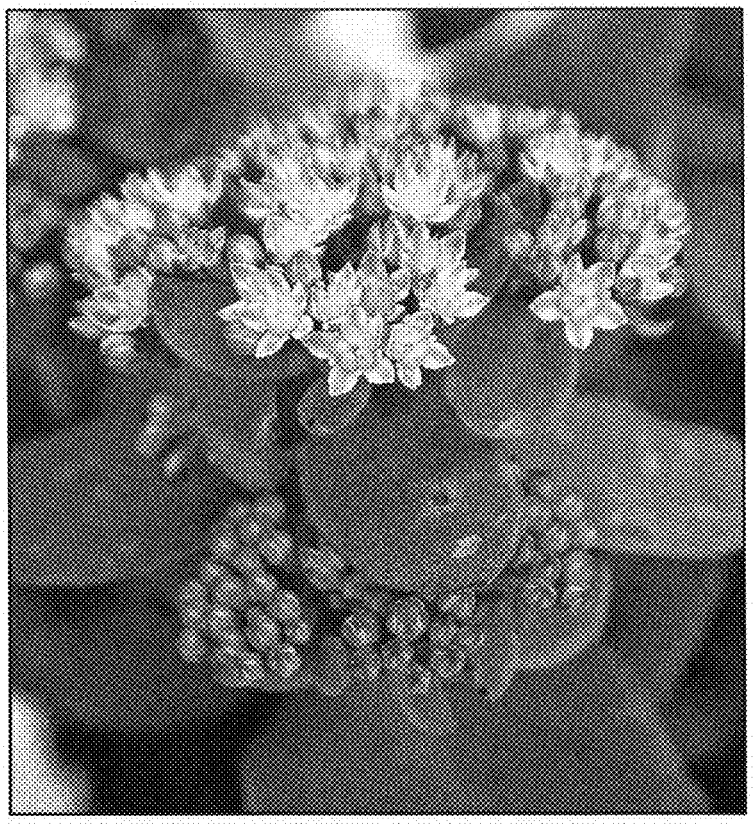
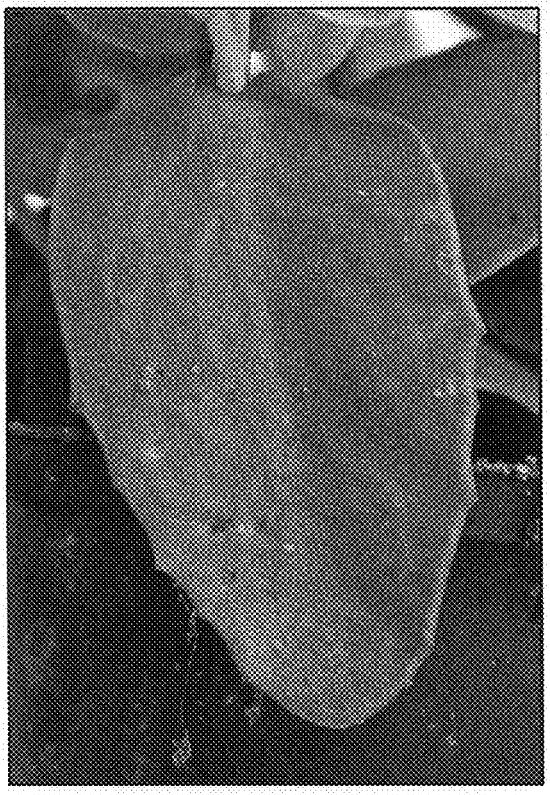

* * * * *